United States Patent [19]

Koupchinov et al.

[11] Patent Number: 5,238,929
[45] Date of Patent: Aug. 24, 1993

[54] CORRECTION OF TRIBOLOGY OF ARTHRITIS-AFFECTED JOINTS AND MEDICINE FOR ITS IMPLEMENTATION

[75] Inventors: Boris I. Koupchinov; Sergey F. Ermakov, both of Gomel; E. D. Belojenko, Minsk; Vladimir G. Rodnenkov, Gomel, all of U.S.S.R.; Vladimir N. Kestelman, Pennsauken, N.J.

[73] Assignee: Development Products, Inc., Pennsauken, N.J.

[21] Appl. No.: 779,490

[22] Filed: Oct. 22, 1991

[51] Int. Cl.$^5$ ............................................ A61K 31/56
[52] U.S. Cl. .................................................... 514/182
[58] Field of Search ........................................ 514/182

[56] References Cited

U.S. PATENT DOCUMENTS 4,212,864  7/1980  Tax ...................................... 514/182
4,569,931  2/1986  Yoshizuka et al. .................. 514/182

FOREIGN PATENT DOCUMENTS 144300  9/1982  Japan .

OTHER PUBLICATIONS

CA 87:465623 Kunitomo et al Suppression of Adjuvant Arthritis in Rats by Cholesterol.

Primary Examiner—Marianne M. Cintins
Assistant Examiner—Rebecca Cook
Attorney, Agent, or Firm—Simpson & Simpson

[57] ABSTRACT

The protection of cartilaginous surfaces against wear by ensuring their low friction despite a deficiency of joint lubrication components. A specific mixture of liquid-crystal cholesterol ester derivatives can be introduced by a variety of means into the affected joints to provide a superior lubrication of the cartilaginous surfaces.

8 Claims, 2 Drawing Sheets

CORRECTION OF TRIBOLOGY OF ARTHRITIS-AFFECTED JOINTS AND MEDICINE FOR ITS IMPLEMENTATION

BACKGROUND OF THE INVENTION

This invention relates to a medicine aimed at the recovery of normal functioning of arthritis-affected joints.

One known method of medical correction of arthritis-affected joints uses "Rumalon" which is based on mucopolysaccharides, peptides as well as amino acids, nucleotides and nucleosides, chondrocides and redcerebrum cells, introduced intramuscularly. This method is beneficial for the recovery processes of cartilaginous tissue since the medicine stimulates the synthesis of mucopolysaccharides and slows down their decomposition. A principal disadvantage of this method is that the medicine can be used only in the form of injections, and provides no lubrication effect.

Another method of treating arthritis-affected joints comprises applications of dimethylsulfoxide (DMSO). DMSO is dissolved in doubly-distilled water together with special medicines and is applied on the skin in the area of affected joint. The compound penetrates the contacting area of cartilages through the undamaged skin and synovial membrane of the joint. This contributes to lessening of the pain syndrome, increasing the scope of the joint motions and lessening edema. Disadvantages of this method are insufficient effectiveness of the joint disfunction compensation and reduction of the pain syndrome, considerably long term of medical treatment, secondary effects of allergy nature and contraindicating; diseases of kidneys and livers, et cetera. This method is not applicable under conditions of deficiency of joint lubrication.

Still another method includes the use of medicine based on a 15% aqueous solution of polyvinylpyrolidone (PVP) introduced into the joints in the form of injections. This method ensures a temporary replenishment of synovia deficiency, contributes to antiphologistic effect and improvement of metabolism in the joint cavity. However, the disadvantage of this method is the impossibility of its implementation other than by intrajoint injections; topical applications have a low penetrating capability through the skin due to a high molecular mass of the medicine (PVP). This medicine is also characterized by insufficient rheological and anti-friction properties which manifest themselves in the following:

1. Constancy of rheological properties of the medicine on the PVP basis and discrepancy between its viscosity and that of natural synovia (the 15% solution of PVP has a viscosity of 1.8 mPa×s), whereas the viscosity of natural synovia depends on the hyaluronic acid contained in it and can vary within a wide range from 5.7 to several hundreds of mPa×s. The viscosity of the natural synovia does not depend on the shearing rate, whereas the PVP-based medicine is characterized by a relatively constant relationship between the viscosity and the shearing rate. Depending on the load, synovia is also capable of changing the viscosity due to the fact that low-molecular components are squeezed out of it and penetrate the cartilaginous tissue. Absence of the viscosity-variation effect under the action of load of the PVP-based medicines brings about their rapid removal from the joint cavity.

2. Low lubrication capability. At friction of cartilages in the presence of PVP-based medicine there is realized a friction coefficient of not less than 0.08, while the joints of a healthy human-being have a friction coefficient of 0.001–0.03, i.e., by an order of magnitude lower.

Still another medication for the medical treatment of arthritis-affected joints comprises a 0.8–4.0% aqueous solution of sodium salt of carboxymethylcellulose and mineral salts contained in the blood plasma. This medicine due to the presence of sodium salt of carboxymethylcellulose with the properties similar to the hyaluronic acid possesses rheological characteristics typical of natural synovia. However, like other known medicines, it has low lubrication properties.

Thus, the common disadvantage of the known art methods of the medical correction of tribology of arthritis-affected joints and the medicines for their implementation is the absence of components contained in them which are responsible for anti-friction characteristics of synovia.

SUMMARY OF THE INVENTION

The object of the invention is the protection of cartilaginous surfaces against wear by ensuring their low friction despite a deficiency of the joint lubrication components. A specific mixture of liquid-crystal cholesterol ester derivatives can be introduced by a variety of means into the affected joints to provide a superior lubrication of the cartilaginous surfaces.

DETAILED DESCRIPTION OF THE INVENTION

Figure 1:
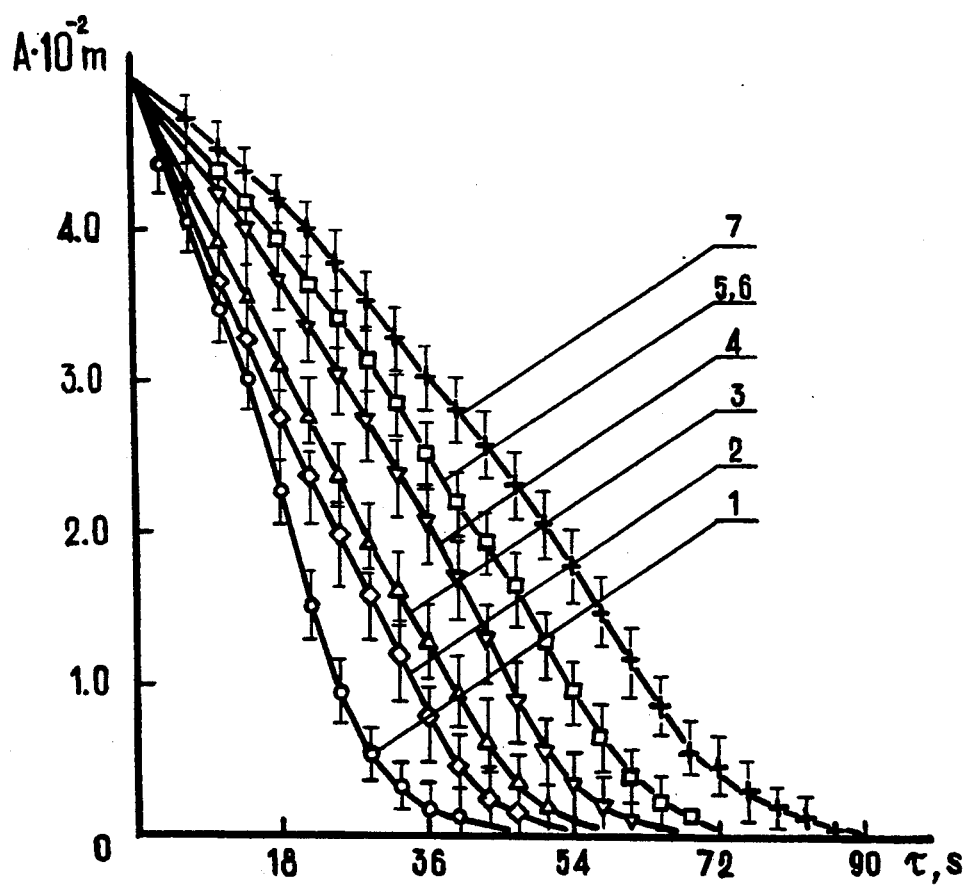
FIG. 1 is a graphical representation of the lubricating effect of the various material used in accordance with the present invention.

The medicine intended for medical correction of tribology of arthritis-affected joints that satisfies the purposes of the present invention comprises a complex mixture of liquid-crystal cholesterol esters of the aliphatic acids: palmitic acid, petroselic acid, linoleic acid, and oleic acid, with the ratio of components being as follows (mass percentage):

| | |
|---|---|
| cholesterolpalmitate | 3 to 5 |
| cholesterolpetroselate | 15 to 35 |
| cholesterollinoleate | 15 to 25 |
| cholesterololeate | balance |

The mixture of cholesterol compounds have a liquid-crystal state within the temperatures corresponding to the transient temperatures from the solid state to the liquid-crystal one (not exceeding 35° C.), and from the liquid-crystal state to the isotropic liquid state (not less than 38° C.).

The medicine is introduced into contact with the contacting, or "rubbing" area of cartilaginous surfaces. The liquid-crystal medicine can be added to solutions of high-molecular weight compounds as described previously in amounts of 0.5 to 1.5 of the mass percentage, and then, by way of injections, the resulting mixture is introduced into the contacting area of cartilaginous surfaces. An example of a useful solution of high-molecular weight compounds comprises 0.5 to 2.5% aqueous solution of the sodium salt of carboxymethylcellulose alone or in combination with an aqueous solution of polyvinylpyrolidone and mineral salts.

The liquid-crystal medicine can also be added to medical oils in amounts of 8 to 10 of the mass percentage, and the medicine is introduced into the contacting area of cartilaginous surfaces by diffusion through applications of the oil mixtures on the area of affected joint. The applications are performed once a day by laying on a warm-up bandage and the procedure is repeated at least 5 to 7 times.

The present invention is based on investigations which have established the presence of cholesterol compounds possessing liquid-crystal properties in the synovial fluid of the human-beings' and animals' joints. The liquid-crystal compounds of cholesterol orient on the surfaces of solid bodies with the long axes of molecules along the microrelief fissures.

In this liquid-crystal state, the cholesterol compounds are capable of considerably reducing friction as compared with petroleum oils used similarly.

The collagen fibers on adjoining surfaces of cartilages become oriented in the direction of prevailing locomotion displacement in the joint, which stimulates the formation of striated microrelief on the cartilaginous surfaces. There is a resemblance of the chemical composition and rheological properties of water-soluble polymers containing pyranose rings and, in particular, the sodium salts of carboxymethylcellulose to the hyaluronic acid responsible for the rheological properties of the natural lubrication components of the joints, i.e., natural synovia.

From these factors, it was surmised that if the joint friction zone, under conditions of "dry joint," (i.e., at a deficiency of the joint lubricant) is contacted with liquid-crystal substances capable of orienting in the microrelief fissures of cartilages and which are in the liquid-crystal state within the temperature range pertaining to the physiological temperatures of animate bodies, i.e., at transient temperatures from the solid state to the liquid-crystal one (not exceeding 35° C.) and from the liquid-crystal state to the isotropic liquid state (at least 38° C.), these substances will ensure the reduction of friction and thus, the protection of the joint surfaces and, consequently, the collagen fibers against wear.

Given below are examples showing the efficiency of the present invention as well as the methods for implementation.

To prepare the medicine having the liquid-crystal state of the lubricant within the temperature range including the physiological temperatures of animate bodies, use is made of cholesterolpalmitate, cholesterolpetroselate, cholesterollinoleate and cholesterololeate which are mixed at the required ratio and heated to the isotropic liquid-state transition temperature. Upon cooling, there is obtained the liquid-crystal medicine with the required temperature range of the liquid-crystal state which is ready for use.

Specific compositions of the liquid-crystal medicine and their temperatures of the liquid-crystal state are given in Table 1.

TABLE 1

Compositions of Liquid-crystal Medicine
Component and its contents, mass percentage

| Variant | cholesterolpalmitate | cholesterolpetroselate | cholesterollinoleate | cholesterololeate | liquid-crystal state temperature °C. |
|---|---|---|---|---|---|
| 1 | 2.0 | 45.0 | 75 | 23.0 | 0–28 |
| 2 | 3.0 | 35.0 | 60 | 37.0 | 12–48 |
| 3 | 4.0 | 25.0 | 45 | 51.0 | 20–55 |
| 4 | 5.0 | 15.0 | 30 | 65.0 | 30–61 |
| 5 | 6.0 | 5.0 | 15 | 79.0 | 38–78 |

As is shown by the table, the following compositions (mass percentage) possess the liquid-crystal state within the temperature ranges corresponding to the physiological temperatures of animate bodies:

| | |
|---|---|
| cholesterolpalmitate | 3 to 5 |
| cholesterolpetroselate | 15 to 35 |
| cholesterollinoleate | 15 to 25 |
| cholesterololeate | Balance |

Addition of these compositions of the liquid-crystal medicine into solutions of high-molecular compounds has been performed as follows.

EXAMPLE 1

The sodium salt of carboxymethylcellulose in amount of 0.5 to 2.5 of mass percentage is preliminarily added into distilled water at room temperature. To the resulting aqueous solution of the sodium salt of carboxymethylcellulose is added the required amount of the liquid-crystal state mixture (0.5 to 1.5 of mass percentage) which had been heated in a drying cabinet to a temperature of 70° to 90° C. Upon melting and transition into the isotropic fluid, the liquid-crystal medicine is added into the aqueous solution of the sodium salt of carboxymethylcellulose while constantly stirring the latter by means of the electric mixer. After the liquid-crystal medicine is uniformly distributed in the aqueous solution, the heating process is stopped and the obtained mixture is cooled at a rate of 2 to 3 degrees/minute with the stirring process being continued until the mixture is cooled to a room temperature to provide a mixture ready for use in the form of injections.

EXAMPLE 2

Preparation of the mixture of high-molecular weight compounds solution and that of the liquid-crystal compound is effected under conditions similar to those of Example 1, the difference being that to the sodium salt of carboxymethylcellulose is added an aqueous solution of polyvinylpyrolidone and mineral salts.

EXAMPLE 3

The cholesterol compound mixture having the desired liquid-crystal state (8 to 10 of the mass percentage) is mixed into medical oils (liquid petrolatum, castor oil and silicone oil), and the resulting mixture is heated to a temperature of 70° to 90° C. Upon cooling, a mixture is obtained ready for use in the form of topical applications.

The rheological properties of normal synovia and the solutions of high-molecular compounds with the liquid-crystal compound intended for injections have been determined at 24° C. The test results are specified in Table 2.

Loading of such a friction pair was effected by varying the mass of pendulum through the use of calibrated

TABLE 2

Test Results of Rheological Properties of Joint Lubricants
Component and its contents, mass percentage

| Variant | liquid-crystal compound | sodium salt of carboxy-methyl cellulose | distilled water | polyvinyl-pyrdidone and mineral salts | Viscosity of compositions, mPa·s, at a shearing rate of s$^{-1}$ | | |
|---|---|---|---|---|---|---|---|
| | | | | | 3.0 | 145.8 | 1312.0 |
| 1 | 0.3 | 2.8 | 96.9 | — | 95.4 | 45.0 | 24.1 |
| 2 | 0.5 | 2.5 | 97.0 | — | 04.7 | 24.1 | 16.2 |
| 3 | 1.0 | 1.5 | 97.5 | — | 54.7 | 16.9 | 7.2 |
| 4 | 1.5 | 0.5 | 98.0 | — | 35.8 | 7.5 | 5.4 |
| 5 | 1.7 | 0.3 | 98.0 | — | 15.1 | 2.4 | 2.4 |
| 6 | 0.3 | 2.8 | — | 96.9 | 96.1 | 46.2 | 25.4 |
| 7 | 0.5 | 2.6 | — | 97.0 | 66.0 | 26.1 | 17.1 |
| 8 | 1.0 | 1.5 | — | 97.5 | 55.0 | 17.5 | 8.0 |
| 9 | 1.5 | 0.5 | — | 98.0 | 36.5 | 9.1 | 67. |
| 10 | 1.7 | 0.3 | — | 98.0 | 16.4 | 2.9 | 2.9 |
| 11 | 15% aqueous solution of PVP | | | | 1.8 | 1.5 | 1.3 |
| 12 | 2% aqueous solution of sodium salt of carboxymethylcellulose | | | | 54.7 | 15.9 | 7.0 |
| 13 | Normal synovial fluid | | | 54.7 | 15.3 | 7.0 |

The investigations show that the best resemblance to the rheological properties of natural synovia are exhibited by the compositions (2-4) whose ingredients include the sodium salt of carboxymethylcellulose, liquid-crystal compound and distilled water with the ratio of components being as follows (mass percentage):

| sodium salt of carboxymethylcellulose | 0.5 to 2.5 |
|---|---|
| liquid-crystal compound | 0.5 to 1.5 |
| distilled water | Balance | as well as to the compositions (7-9) whose ingredients include the sodium salt of carboxymethylcellulose, liquid-crystal compound and aqueous PVP+mineral salts with the ratio of components being as follows (mass percentage):

| sodium salt of carboxymethylcellulose | 0.5 to 2.5 |
|---|---|
| liquid-crystal compound | 0.5 to 1.5 |
| PVP + salts (aqueous) | Balance |

Compositions 3 and 8 have the best correspondence to the rheological properties of natural synovia.

The tribological investigations have been performed with the use of a pendulum-type tribometer which duplicates locomotion typical of the natural joint. As far as the anatomical structure is concerned, the humerus joint is the most suitable for investigations with the use of the pendulum-type tribometer. The samples for friction have been manufactured of the humerus bone head (convex portion) and the scapula joint depressions (concave portion) of animals 1 to 2 hours after they were slaughtered. For each experiment, there were manufactured at least three samples and the cartilage was not separated from the bone subject to investigation.

With the purpose of simulating "dry joints," i.e., to remove low-molecular synovial components from the joint cartilages and, consequently, to eliminate their effect on the results of experiments, all the samples were steeped before the test in distilled water for 24 hours and then, dried with the use of filtering paper and subjected to test.

The humerus bone head (convex portion) was attached to the pendulum and installed into the scapula joint depression which was secured to the rigid base.

weights. For the purpose of correlation of the test results in all the experiments, the contacting area of cartilage was set constant and evaluated by carrying over, at contact, the water-soluble paint from the previously painted surface of the cartilage to unpainted surface of its adjoining cartilage. The frictional force was judged by the pendulum oscillations damping as well as by the tilting angle to the X-axis showing the relationship between the amplitude of oscillations and the time. The initial amplitude of oscillations in all the experiments remained constant. Prior to the test, 1 cm$^3$ of lubrication medium was introduced into the joint under test.

Used as the lubrication medium were the known compounds for the medical correction of joints, namely: the 15% aqueous solution of PVP and 0.8 to 4.0% aqueous solution of the sodium salt of carboxymethylcellulose. The obtained results were compared with the results for natural synovia with the contents of total cholesterol being 0.9 mmol/l and 4.09 mmol/l, as well as for aqueous solution of PVP and mineral salts and the 0.5 to 2/5% aqueous solution of the sodium salt of carboxymethylcellulose both without and with the admixtures of the liquid-crystal compound.

FIG. 1 demonstrates graphically the kinetics of variation of amplitude of the tribometer pendulum oscillations in case of presence of the following media in the joint under test:

1. aqueous PVP+mineral salts (hemodesis);
2. 15% aqueous solution of PVP;
3. 2% aqueous solution of the sodium salt of carboxymethylcellulose;
4. hemodesis with the 1% admixture of the liquid-crystal compound;
5. 2% aqueous solution of the sodium salt of carboxymethylcellulose with the 1% admixture of the liquid-crystal compound;
6. synovial fluid with the contents of total cholesterol being 0.9 mmol/l;
7. synovial fluid with the contents of total cholesterol being 4.09 mmol/l.

The results presented in FIG. 1 show that introduction of the liquid-crystal compound in amount of 1 mass percentage into the aqueous solution of the sodium salt of carboxymethylcellulose ensures the same friction value as the synovial fluid with the smaller contents of the total cholesterol (curve 5, 6). Considerable reduction in the friction of cartilages is also noted for the PVP +mineral salts (hemodesis) containing the liquid-crystal compound (curve 4). It is also noted that for the synovial medium with increased contents of cholesterol, the time of the pendulum oscillation damping is increased (curve 7). From the results presented in FIG. 1, it is obvious that introduction of the liquid-crystal mixture, i.e., the cholesterol derivative having the desired liquid-crystal, into the known compounds used for the medical correction of joints brings about a significant improvement of their tribological properties. A decrease in concentration of the liquid-crystal compound below 0.5% leads to deterioration of their tribological properties, while an increase of the concentration above 1.5% causes sedimentation of the liquid-crystal compound. Consequently, concentration of the cholesterol blending in amounts of 0.5 to 1.5 of the mass percentage is the optimum, i.e., the concentration at which the best tribological properties are obtained. Thus, the investigations have shown that the properties of synovial medium of the joints to ensure a low friction of the adjoining cartilages are associated with the presence of the cholesterol blending in this medium which possess the liquid-crystal properties within the temperature range including the temperature of the human body.

In experiments performed on ten male rats (herdbred) taken from the Leningrad experimental nursery "Rappalovo" of the Medical Academy of Science of the USSR, there was studied the effect of these liquid-crystal compounds of cholesterol on the joint cartilage in the case of adjuvant arthritis. The disease was caused following the Beneke and Nhol procedure. The animals were subdivided into two groups: control (5) and experimental (5). The investigation was carried out between the 14th–21st days in the presence of obvious inflammation changes in the joints. In the experimental group, the animals were given the cholesterol liquid-crystal compounds injected into the joint at the contacting area of cartilages. The animals of both groups were taken out of the experiment seven days after the experiment had begun. From the investigated joints, there were made the total histological compounds in the sagittal plane which were painted with hematoxylineosin. It was established that in the control group, there were noted the irregularity of the cartilaginous tissue width, non-uniformity of painting (metachromatic state of the cartilage main substance), fibrous structure of the cartilage surface along the outer edge, its spontaneous fragmentation and presence of wasting-away of bone and tissue filled with conjunctive tissue. Upon introduction of the cholesterol liquid-crystal compounds, in the experimental group there was retained a similar width of the cartilaginous tissue, noted the irregularity of distribution of the cell elements and pale color of painting of the intermediate substance; however, the dystrophical changes were expressed more weakly than in the test group. This picture has testified to the protection role of the cholesterol liquid-crystal compounds when injected into the friction zone of pathologically changed cartilage.

Taking into consideration the fact that transportation of the liquid-crystal substances to the affected joint is desirably performed through the skin, investigations were conducted of the diffusion capability of the cholesterol liquid-crystal compounds through the skin of a human-being taken from a corpse or during an operation (amputation of a limb). Used during investigation were the 8 to 10% solution of these liquid-crystal compounds of cholesterol in medical oils (liquid petrolatum, castor oil and silicone oil) since they are widely used in the medicine and give no side effects.

The appliance used for investigating the diffusion was essentially a glass accommodating a glass cylinder to which lower end face there was secured a piece of skin. The cylinder was installed at some distance from the glass bottom so that it became slightly immersed into the solution of the cholesterol liquid-crystal compounds in the liquid petrolatum which was poured into the glass. Arranged above the skin in the cylinder was the tested medical oil without admixtures of the liquid-crystal compounds whose samples were periodically taken and analyzed for presence of the cholesterol liquid-crystal compounds with the use of spectrophotometer by variation in the optical density of the absorption band within a region of $1750^{-1}$ which is typical for oscillations of the oxygen atom in the ester bond. The investigation of diffusion has been performed at $t=36.7°$ C. The analysis of the test results presented in Table 3 shows that the diffusion capability of the selected liquid-crystal compounds of cholesterol through the skin is satisfactory and will permit penetration into the joint.

TABLE 3

Test Results of Diffusion of the Cholesterol Liquid-crystal Compounds (LCC)

| Time of taking the samples | Concentration of cholesterol LCC |
|---|---|
| Within 24 hours | 0.5262 |
| Within 48 hours | 3.7055 |
| Within 72 hours | 7.7490 |
| Within 96 hours | 9.6040 |

Additional experiments were performed on the animals to study the diffusion capability of the cholesterol LCC through the skin and the possibility of intrajoint transportation. For this purpose, there were taken 26 male rats (herd-bred) from the Leningrad experimental nursery "Rappalovo" of the Medical Academy of Science of the USSR, each weighing 265 to 290 g. The animals were subdivided into two groups. In the first group (12 rats), the cholesterol (LCC) diffusion was investigated under conditions of physiological standard. In the second group (12 rats), there was simulated the arthritis of joints of the lower left limb by injecting 0.1 ml. of the Freind adjuvant under the sub-sole aponeurosis following the Beneke and Nhol procedure. The investigation was carried out between the 14th and 21st days in the presence of obvious inflammation changes in the joints.

The compound under test was a mixture of suggested cholesterol (LCC) labeled as $1.2^3$ N (radioactivity of compound is $7.5\pm0.5\times10^6$ of decays/mg.$\times$min. with the liquid petrolatum. The animals were given daily applications of newly prepared compound on the area of the left knee joint in the amount of 0.5 ml. with an exposition of 60 min. under the hydrobutyrate narcosis. At the end of the procedure, the joint area was wiped with a chloroform and water so as to avoid entering of the compound into the alimentary canal and to avoid errors in the experiment. The animals were taken out of the experiment by three rats in each group within 1, 3, 5, 7 days after one-, three-, five- and seven-time applications, respectively.

Samples of the following tissues were subjected to investigation: blood, liver, kidneys, front-side sections of the left knee joint capsule and the joint cartilage of the femur condyles. The radioactivity of the compounds was determined using the liquid scintillation method. The homogenized, solubilized and labeled ($^3N$) tissue was transferred to special counting flasks which were filled with the scintillation mixture toluene+PPO (7 g/l)+POOOP (0.075 g/l). The radioactivity of the compound was determined by the number of decays per minute. By dividing the compound true radioactivity value by the tissue weighed portion (mg.), there was obtained a specific radioactivity (SR) of the compound expressed by decays/min.×mg. of tissue; each SR value was determined after two- or three-time repetitive checks. To determine a relative specific radioactivity (RSR), the SR of the tissue compound was compared with that of the introduced radioactive substance and expressed in percents.

The test results (SR) under conditions of the physiological standard (group 1) and in the case of adjuvant arthritis (group 2) are given in Table 4, below. They testify to the presence of the intrajoint transportation of the cholesterol esters by diffusion through the skin; in the case of adjuvant arthritis, the diffusion capability was much greater.

The analysis of the RSR compounds of the joint cartilage and the joint capsule at applications of the tested cholesterol LCC compound on the tail area of two animals being not additionally narcotized has also revealed a statistically true increase of the cholesterol LCC contents in the joint tissues in the case of adjuvant arthritis as compared with the animals under conditions of the physiological standard. The maximum of the radioactive substance contents in the joint cartilage was observed within five days in the case of adjuvant arthritis and seven days, in the case of healthy rats (in the area of the joint capsule), and within three days—of both groups.

Hence, the above-mentioned investigations testify to a high-diffusion capability of the cholesterol LCC through the skin into the affected joint area; it means that they form a real basis for the medical means used for medical correction of tribology of degeneratively changed joints which are introduced into the contacting area of cartilages through diffusion.

moval or the minimum effect of the natural lubricants. The effectiveness of medical treatment was evaluated according to the universally adopted clinical symptoms (lessening of crunching, pain syndrome, toughness and improvement of motions) which are widely used in such investigations.

The tested group of patients was subjected to the medical treatment by way of applications of the cholesterol LCC solution, in the amount of 10 of the mass percentage, in the liquid petrolutum. The applications were made for ten days on the affected joint once a 24-hour period with the subsequent laying of the warm-up bandage.

In the second group (control group of patients No. 1) of patients, there were used the application of the 50% solution of dimethylsulfoxide (DMSO) daily for ten days.

The third group of patients (control group of patients No. 2) received the "placebo" (applications of pure liquid petrolatum).

The fourth group of patients (control group of patients No. 3) was subjected to the medical treatment following the universally adopted procedure (applications of paraffin, ultrasonic vibrations, massage).

Figure 2:
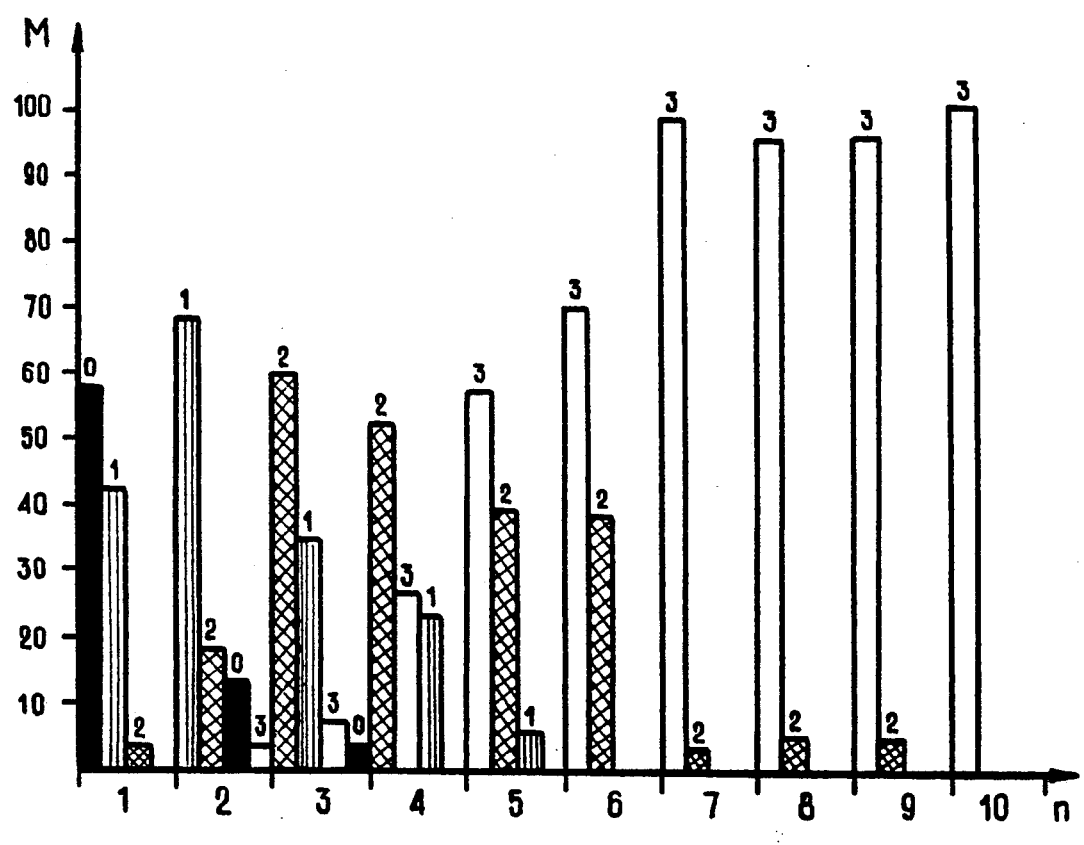
FIG. 2 is a bar graph illustrating the improvements obtained in accordance with the present invention for topical application.

As a result of the carried-out clinical investigations performed in the group under test, there were noted complete disappearance of the joint edema, increasing of the skin temperature, complete disappearance of the pain feelings at rest and in motions, increasing of the active painless bending of the joint at 15° on the average. The disappearance of edema and increasing of the skin temperature indirectly indicated to improvement of the blood microcirculation. The maximum effectiveness was revealed upon 5 to 7 procedures. The results of these investigations are shown in FIG. 2, where: M—number of observations in percents; n—number of procedures; 0—absence of effect; 1—insignificant effectiveness; 2—average effectiveness; 3—considerable effectiveness of the procedure.

In control group No. 1 upon using the applications of DMSO, there was noted lessening of the joint edema, in most cases (62.5%) there disappeared pains at rest, considerably reduced the intensity of pain syndrome in motions (72.7%); however, in all the cases there were retained the pain feelings at a maximum loading of the joint and when the patients were using a staircase in this

TABLE 4

Results of Radioisotope Investigation of Diffusion Capability of the Cholesterol LCC, labeled as $1.2^3$ N Through the Skins of Rats Under Conditions of Physiological Standard (gr. 1) and in the Case of Adjuvant Arthritis (gr. 2)

| Specific radioactivity of compound (decays/min. × mg.); Time taken for experiment (24 hours) | | Joint cartilage | Joint capsule | Liver | Kidneys | Blood |
|---|---|---|---|---|---|---|
| 1 | Gr. 1 | 3.38 ± 0.8 | 4.55 ± 0.5 | 5.93 ± 1.22 | 3.69 ± 0.4 | 558.9 ± 150 |
|   | Gr. 2 | 19.6 ± 16 | 36.5 ± 20 | 35.2 ± 17 | 33.99 ± 13 | 974.2 ± 420 |
| 3 | Gr. 1 | 4.23 ± 3.0 | 3.94 ± 1.5 | 7.61 ± 0.46 | 2.95 ± 8.0 | 621 ± 210 |
|   | Gr. 2 | 32.32 ± 17 | 43.2 ± 21 | 52.8 ± 9.0 | 31.57 ± 8.0 | 288 ± 135 |
| 5 | Gr. 1 | 7.52 ± 4.0 | 9.02 ± 3.0 | 26.41 ± 2.4 | 24.6 ± 14 | 721.93 ± 3 |
|   | Gr. 2 | 33.34 ± 16 | 28.13 ± 0.4 | 80.13 ± 0.4 | 42.8 ± 17 | 293.7 ± 14 |
| 7 | Gr. 1 | 13.8 ± 6.0 | 5.02 ± 3.0 | 24.65 ± 4.7 | 73.3 ± 40 | 1266.77 ± |
|   | Gr. 2 | 5.5 ± 3.0 | 28.9 ± 13 | 36.4 ± 2.0 | 24.52 ± 7.0 | 293.7 ± 14 |

The medical effectiveness of the suggested method was revealed on four groups of patients having approximately the same nature of disease. When selecting the patients, the obligatory condition was the absence of exudation symptoms in the joints, i.e., complete reconnection, the scope of motions in the joints within the painless limits has increased by 5 to 10% in five cases out of eleven.

In control group No. 3 to achieve the analogous effectiveness there were required 20 to 25 procedures In control group No. 2 no effectiveness as a result of using "placebo" (applications of pure liquid petrolatum) was revealed.

Thus, the carried-out clinical and experimental investigations provide a strong evidence that the suggested method of medical correction of arthritis-affected joints and the compound for its implementation as a result of penetration of the cholesterol LCC into the contacting area of cartilages as well as realization of the friction and wear mechanism inherent to the natural synovial medium of the joints possess the increased effectiveness as compared with the known art methods and medicines used the medical treatment of degenerativedystrophical diseases of joints.

What is claimed is:

1. A method for the treatment of tribology of arthritis-affected joints in a warm-blooded animals comprising introducing into the afflicted joint of said animal an effective amount of a cholesterol ester pharmaceutical composition which is in the liquid-crystal state at the physiological temperature of the joint being treated, said cholesterol ester composition characterized by a maximum transition temperature from the solid state to the liquid-crystal state of 35° C. and a minimum transition temperature from the liquid-crystal state to the isotrophic liquid state of at least 38° C., said cholesterol ester composition comprising 3% to 15% by weight of cholesterolpalmitate, 15% to 25% by weight of cholesterolpetroselate, 15% to 25% by weight of cholesterol-linoleate and the balance is cholesterololeate.

2. A method in accordance with claim 1 in which said cholesterol ester composition is introduced into said joint by injection in an aqueous solution containing from 0.5% to 2.5% aqueous salt of carboxymethylcellulose, said liquid-crystal composition being present in the range of about 0.5 to 1.5 of the mass percentage.

3. A method in accordance with claim 2 in which said aqueous solution additionally contains polyvinylpyrolidone and mineral salts.

4. A method in accordance with claim 1 in which said liquid-crystal composition is incorporated in a medical oil in the amount of 8 to 10 mass percentage and is introduced into the joint by diffusion through the application of the mixture in the area of the affected joints being treated.

5. A pharmaceutical composition for the treatment of tribology of arthritis—affected joints in a warm-blooded animal comprising 3% to 15% by weight cholesterolpalmitate, 15% to 35% by weight of cholesterol-petroselate, 15 to 25% cholesterol-inoleate and the balance comprising cholesterololeate, said mixture of cholesterol esters having a maximum transition temperature from the solid state to the liquid-crystal state of 35° C. and a minimum transition temperature from the liquid-crystal state to the isotrophic liquid state of at least 38° C.

6. A composition in accordance with claim 5 comprising from 8 to 10 mass percentage of said cholesterol ester composition, the balance being a medicinal oil.

7. A composition in accordance with claim 5 in which said cholesterol ester composition comprises from about 0.5 to 1.5 mass percentage of an aqueous solution and said aqueous solution also contains from 0.5% to 2.5% of the sodium salt of carboxymethylcellulose.

8. A composition in accordance with claim 7 in which said aqueous solution additionally contains polyvinylpyrolidone.

* * * * *